Figure 2:
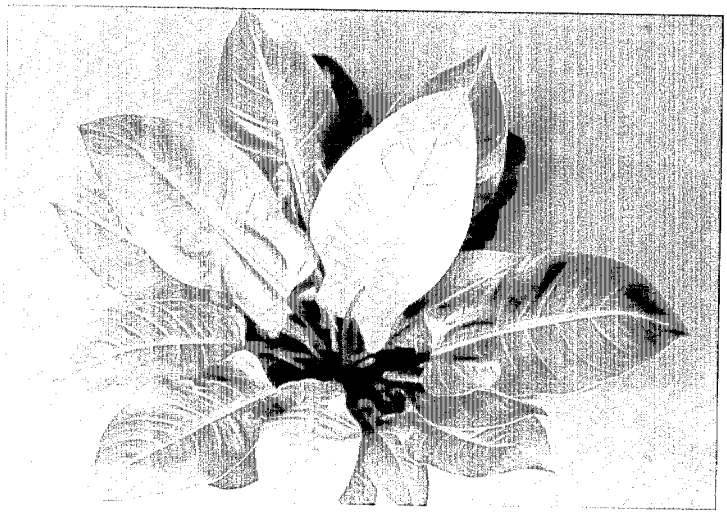

United States Patent [19]

Miller

[11] Patent Number: Plant 6,797

[45] Date of Patent: May 16, 1989

[54] PHILODENDRON PLANT NAMED PRINCE OF ORANGE

[75] Inventor: Howard N. Miller, Gainesville, Fla.

[73] Assignee: Cora McColley, Orlando, Fla.

[21] Appl. No.: 146,777

[22] Filed: Jan. 21, 1988

[51] Int. Cl.[4] ..... A01H 5/00
[52] U.S. Cl. ..... Plt./88
[58] Field of Search ..... Plt. 88

*Primary Examiner*—Robert E. Bagwill
*Attorney, Agent, or Firm*—Frank B. Robb

[57] ABSTRACT

There is disclosed a stocky, compact self-heading Philodendron plant of unique color, having new leaves of bright orange, which when the leaves mature change colors from orange to apricot, to yellow green to pale or medium green, pinkish red petioles adding to the overall distinctive color of the plant wherein the petioles are short and stocky averaging six to seven inches in length, whorls of twelve inch long by eight inch wide leaves that are elliptic to ovate in shape coming from the crown, a relatively high indoor light intensity and moderate temperature being needed for good color.

2 Drawing Sheets

BACKGROUND AND DESCRIPTION OF THE INVENTION

My present invention comprises a new and distinct cultivar of Philodendron plant which is the result of crossing a yellow-green seedling from the breeding line which I have designated 6634-14, with an unnamed seedling whose parentage includes *Philodendron domesticum, Philodendron erubescens, Philodendron wendlandii* and *Philodendron imbe.* A selection from this cross was in turn crossed with the species *Philodendron cannifolium* to shorten and thicken the petioles and to give the plant a true rosette growth habit. From this cross a single seedling was selected for propagation and is the embodiment of this invention.

An extensive program of philodendron hybridization is being carried on in the vicinity of Orlando, Fla., with much of the effort directed toward developing tough, leathery, Philodendron which are compact, self-heading, excellent growers and keepers under in-house environments.

With the increasing emphasis on interior landscaping, there is great demand for new types of Philodendron with distinctive color, form and growth habit. The on-going breeding program has these objectives as a goal. The philodendron of the instant invention is a compact self-heading plant of distinctive form, leaf type and color which emphasizes many of the above objectives. I have chosen to call it "Prince of Orange" for commercial identification.

I have caused the new variety to be asexually reproduced from crown off-shoots. Since the plant is compact, self-heading, and essentially has no stem, vegetative propagation is not commercially feasible. The plant can be mass produced by tissue culturing, and has been found to retain its distinctive characteristics through successive asexual reproduction.

My new variety has been grown under various conditions in several locations and has maintained its form and color under a light range of 1000–1800 foot candles and a temperature range of 60–90 degrees F. At very high temperatures the glossy-orange color may become a dull yellow bronze. This same color change may result from very high light intensities, and is opposed to the concept for which it was developed, which was for its intense bright-orange color that is much in demand by interior plantscrapers. The plant grows well under moderate in-house conditions.

The plant, because of its unique color, is very distinct from other philodendrons in cultivation and is not described by Graf, Bailey or Das Pflanzenreich. While my new variety has some of the characteristics of certain species and hybrids, in most respects it is substantially different as comparisons with other varieties disclose.

Philodendron "Prince of Orange" can certainly be described as colorful. The new leaves are a glossy, bright orange, and as the leaves mature, they change color from orange to apricot to yellow-green to pale or medium green. The pinkish-red petioles add to the overall color of the plant. The plant is a compact rosette with short thick petioles arising in a whorl from a crown or short stalk. There are other differences which are noted hereinafter and further distinguish this cultivar.

The new variety is also visually distinguished by shape of the leaves, the mature leaves being narrowly ovate with hastate base and acute tip. The mature leaves are restricted at the base and the margins are entire. Pinnate venation with large flattened midribs are notable as are the thick, leathery, glossy, orange, apricot, yellow-green leaves. The width of the leaf is approximately one half the length.

The petioles are erect to semi-erect, round with flat slightly concaved upper surface. They are approximately half the length of the leaves, and are a pink-red color. The internodes are one half inch or less.

Since my new variety is a true rosette and essentially without a stem, it is compact. Growth is uniform and of good substance, and under good growing conditions, medium light intensity, good humidity and moderate temperatures, is fast, but the plant does not become leggy or lose its bright orange color. The average height of a year old plant is 18″–20″ with a width of 36″.

The growth of the plant indoors is good. It tolerates air-conditioning and infrequent watering and fertilizing. If provided with adequate light it retains its form and color. The plant performs best under normal in-house conditions with minimum care. Over-watering is detrimental.

This new variety is resistant to bacterial leaf rot and fungal leaf spot. It does not appear to be affected by physiological problems which are troublesome in earlier Philodendron varieties.

Figure 1:
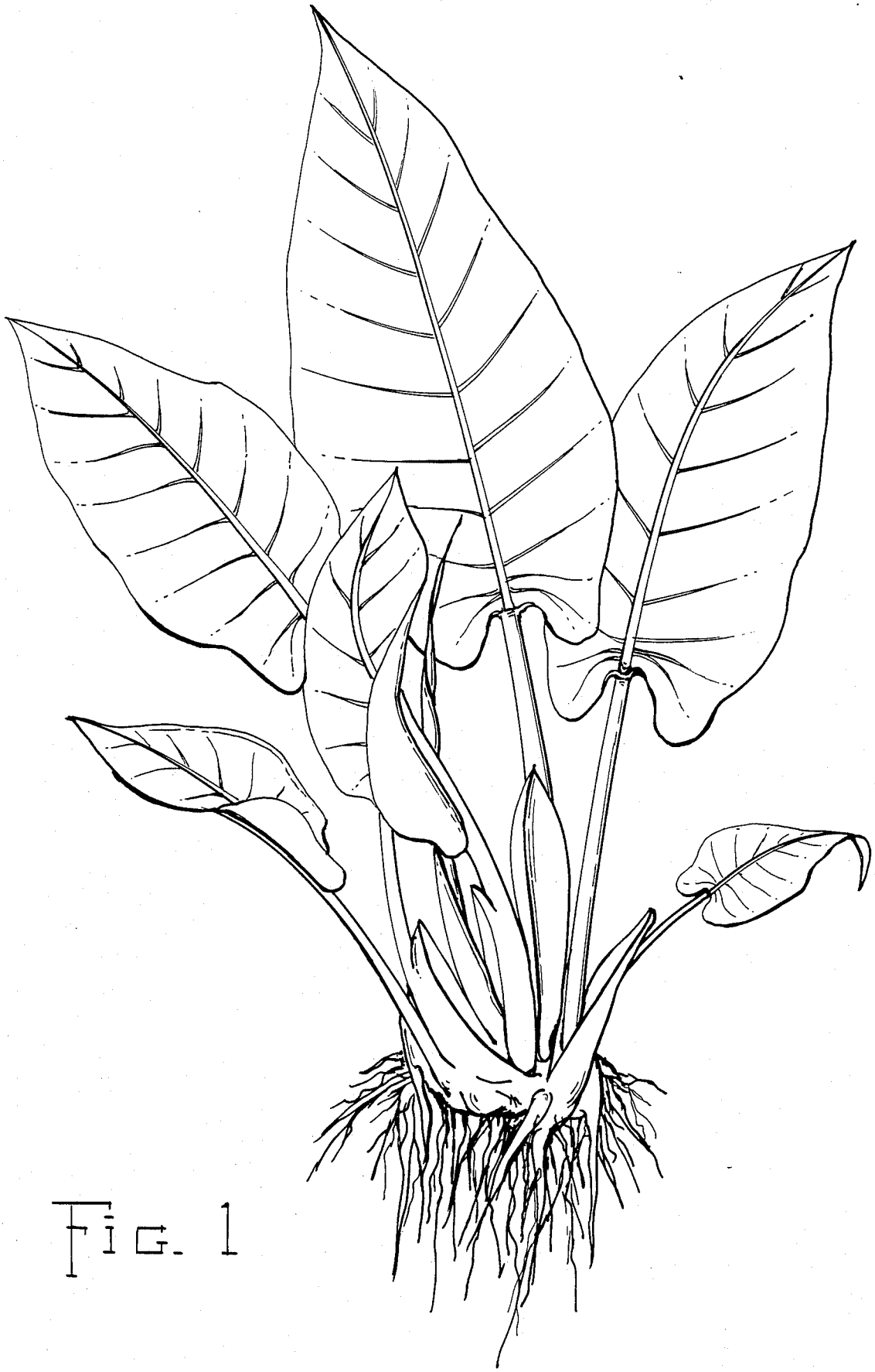

The accompanying drawings forming a part of this disclosure, show a typical plant of the new variety in black and white in FIG. 1 and in color in FIG. 2 with the colors being as nearly true as is reasonably possible to make the same in color illustrations of this character.

Color references are made to the Munsell Color Cascade published by MacBeth Division of Kollmorgen Company, with observations recorded by daylight illumination under vinyl of not more than thirty percent shade.

FORM CHARACTERISTICS

Leaf shape:
- *Mature and immature.*—Narrowly ovate.
- *Tip.*—Acute.
- *Base.*—Mature and immature — hastate.
- *Displacement.*—Smooth to undulate.
- *Margin.*—Entire.
- *Venation.*—Pinnate-sunken.

Leaf attachment: Petiolate.

Leaf arrangement: Closely alternate.

Petiole: Half leaf length; semi-erect to erect; round; upper surface flat; slightly concave.

Stem: Very short-stocky.

Overall appearance: Compact; self-heading, true rosette.

LEAF TEXTURE CHARACTERISTICS

Firm, leathery, glossy.

SIZE CHARACTERISTICS OF TYPICAL MATURE PLANT

Leaf:
- *Width-widest point.*—7"-8".
- *Width.*—1" from tip.—2"-2½".
- *Length.*—12"-14".
- *Thickness.*—0.10 cm.

Petioles:
- *Length.*—6"-7".
- *Diameter (center).*—½".
- *Internode spacing.*—½".
- *Stem diameter.*—1"-1½".

COLOR CHARACTERISTICS

Leaf: (mature) bottom of plant:
- *Top.*—21-13 pale olive green.
- *Bottom.*—21-9 yellow green.

Leaf (mature) center of plant:
- *Top.*—31-13 apricot (red-orange).
- *Bottom.*—36-14.

Leaf (immature):
- *Top.*—*33*-12 Orange.
- *Bottom.*—37-5 Pink.

Leaf venation:
- *Midrib.*—37-5 Pink.
- *Veins.*—37-5 Pink.

Stem: 33-15 Dark red.

Petioles: 37-18 Pink red.

I claim:

1. A new and distinct variety of Philodendron plant, substantially as herein shown and described, characterized as to novelty by its stocky, compact, self-heading growth habit, its unique color of new leaves which are bright, glossy orange, and as the leaves mature changing colors from bright orange, to apricot to pale yellow-green, with pinkish-red petioles which add to the attractiveness of the plant, a whorl of twelve inch long by eight inch wide leaves that are narrowly ovate extending from the crown, relatively high light intensities and moderate temperatures making the plant a very colorful indoor specimen with low maintenance requirements in which the symmetrical growth is upright and attains an average height of eighteen inches to twenty inches and width of thirty-six inches in approximately one year from a tissue culture liner.

* * * * *